United States Patent [19]

Eaton et al.

[11] Patent Number: 4,800,157

[45] Date of Patent: Jan. 24, 1989

[54] PROCESS FOR PRODUCING THE A-21978C ANTIBIOTICS

[75] Inventors: Tom E. Eaton, Greenwood; Lynda M. Ford, Indianapolis; Otis W. Godfrey, Jr., Greenwood; Mary L. B. Huber, Danville; Milton J. Zmijewski, Jr., Carmel, all of Ind.

[73] Assignee: Eli Lilly and Company, Indianapolis, Ind.

[21] Appl. No.: 773,916

[22] Filed: Sep. 9, 1985

[51] Int. Cl.$^4$ .................... C12P 21/04; C12N 1/20; C12R 1/465

[52] U.S. Cl. ........................... 435/71; 435/253; 435/886

[58] Field of Search ............... 435/71, 253, 886

[56] References Cited

U.S. PATENT DOCUMENTS

| Re. 31,396 | 9/1983 | Hamill et al. | 435/71 X |
|---|---|---|---|
| Re. 32,333 | 1/1987 | Hamill et al. | 435/71 X |
| 4,208,403 | 6/1980 | Hamill et al. | 435/71 X |
| 4,331,594 | 5/1982 | Hamill et al. | 435/71 X |
| 4,522,919 | 6/1985 | Shreve et al. | 435/119 |
| 4,524,135 | 6/1985 | Abbott et al. | 435/71 X |

OTHER PUBLICATIONS

Elmder et al., 1977 Genetics of Industrial Microorganisms in Annual Reports on Fermentation Processes, vol. I, Perlman (ed.) Academic Press, N.Y.

*Primary Examiner*—Thomas G. Wiseman
*Assistant Examiner*—Richard C. Peet
*Attorney, Agent, or Firm*—Nancy J. Harrison; Leroy Whitaker

[57] ABSTRACT

Improved fermentation process for producing the gram-positive A-21978C antibiotics which comprises cultivating a new strain of *Streptomyces roseosporus*, NRRL 15998, and the biologically purified culture of this microorganism are provided.

11 Claims, No Drawings

PROCESS FOR PRODUCING THE A-21978C ANTIBIOTICS

SUMMARY OF THE INVENTION

This invention relates to a new microorganism, *Streptomyces roseosporus* NRRL 15998, which produces the A-21978C antibiotics. This invention also relates to an improved process for producing the A-21978C antibiotics by culturing the novel strain of *Streptomyces roseosporus*, NRRL 15998, under submerged aerobic fermentation conditions until a substantial level of the A-21978C antibiotics is produced. The A-21978C antibiotic complex is extracted from the fermentation broth and from the mycelium with polar organic solvents. The A-21978C individual factors are separated and further purified by techniques such as column chromatography.

The A-21978C antibiotics produced by this method are excellent antibacterial agents.

DETAILED DESCRIPTION OF THE INVENTION

Improved methods for producing antibiotics are of great importance. Commonly, the culture isolated from the natural state (the "wild type") produces the antibiotic in low yield. Often, antibiotic production is erratic. Strains with enhanced potency and strains which consistently produce the antibiotic are, therefore, of great value.

This invention provides a greatly improved process for preparing the A-21978C antibiotics by culturing an A-21978C-producing strain of *Streptomyces roseosporus* NRRL 15998 under submerged aerobic conditions in a suitable culture medium until substantial antibiotic activity is produced. The A-21978C antibiotic complex is recovered using various isolation and purification procedures understood in the art.

The A-21978C antibiotics are described by Robert L. Hamill and Marvin M. Hoehn in U.S. Pat. No. 4,331,594. The A-21978C antibiotic complex consists of individual A-21978C factors $C_0$, $C_1$, $C_2$, $C_3$, $C_4$ and $C_5$. The A-21978C complex and the individual A-21978C factors are antibacterial agents which are especially active against gram-positive bacteria.

The Microorganism

The microorganism of this invention has been designated A21978.65. This strain was developed by strain selection and mutation from a culture designated A-21978.6. The A-21978.6 strain, which was studied and characterized by Frederick P. Mertz and Ralph E. Kastner of the Lilly Research Laboratories, was in turn developed from a parent strain isolated from soil from Mount Ararat in Turkey. The A-21978.6 strain was classified as a novel strain of *Streptomyces roseosporus*, Falcão de Morias and Daliá Maia 1961. This classification was made after comparison with published descriptions [R. E. Buchanan and N. E. Gibbons, "Bergey's Manual of Determinative Bacteriology," The Williams and Wilkins Company, 8th Ed., 1974; and E. B. Shirling and D. Gottlieb, "Cooperative Description of Type Strains of Streptomyces," *Intern. Journal of Systematic Bacteriol.*, 808–809 (1972)].

The classification was based on methods recommended for the International Streptomyces Project [E. B. Shirling and D. Gottlieb, "Methods of Characterization of Streptomyces Species," *Intern. Journal of Systematic Bacteriol.* 16, 313–340 (1966)] along with certain supplementary tests. Carbon utilization was determined on ISP #9 basal medium to which carbon sources were added to equal a final concentration of 1.0%. The carbon sources were sterilized by filtration; the basal medium was sterilized by autoclaving. Plates were read after 14 days incubation at 30° C. The cell-wall sugars were determined using a modification of the procedure of Lechevalier, (M. P. Lechevalier, "Chemical Methods as Criteria for the Separation of Actinomycetes into Genera," Workshop sponsored by the Subcommittee on Actinomycetes of the American Society of Microbiology, Dr. Thomas G. Pridham, Convenor; held at the Institute of Microbiology, Rutgers University, The State University of New Jersey, New Brunswick, N.J., 1971.)

The isomer of diaminopimelic acid was determined using the method of Becker et al. [B. Becker, et al., "Rapid Differentiation Between Norcardia and Streptomyces by Paper Chromatography of Whole Cell Hydrolysates," *Appl. Microbiol.* 11, 421–423 (1964)]. Amino acid analysis was determined with washed cell-wall fragments. Melanoid pigments were determined using ISP #1 (tryptone-yeast extract broth), ISP #6 (peptone-yeast extract iron agar), ISP #7 (tyrosine agar), ISP #7 modified (ISP #7 without tyrosine), and a tyrosine assay [Yuzuru Mikami, et al., "Modified Arai and Mikani Melanin Formation Test of Streptomyces," *Intern. Journal of Systematic Bacteriol.* 27(3), 290 (1977)]. Starch hydrolysis was determined by testing for the presence of starch with iodine.

Temperature range, NaCl tolerance, pH range, and antibiotic sensitivity were done using ISP #2 agar medium. The range of temperatures were: 25°, 28°, 30°, 34°, 37°, 40°, 45°, 50° and 55° C. NaCl tolerance was measured by adding NaCl to the agar to equal: 0, 1, 2, 3, 4, 5, 6, 8, 10 and 12%. These were incubated at 30° C. The pH range was measured by adjusting the agar from pH 3.0 to 11.0 at increments of 1.0 pH units, just prior to pouring. Antibiotic sensitivity was determined using sensitivity discs padded onto seeded agar plates.

Color names were assigned according to the ISCC-NBS method (K. L. Kelly and D. B. Judd, "The ISCC-NBS Methods of Designating Colors and a Dictionary of Color Names," U.S. Department of Commerce Circ. 553, Washington, D.C., 1955).

Figures in parentheses refer to the Tresner and Backus color series [H. D. Tresner, and E. J. Backus, "System of Color Wheels for Streptomycete Taxonomy," *Appl. Microbiol.* 11, 335–338 (1956)]. Color tab designations are underlined. The Maerz and Paul color blocks are enclosed in brackets (A. Maerz and M. R. Paul, "Dictionary of Color," McGraw-Hill Book Company, Inc. New York, N.Y., 1950).

Morphology

The morphology of culture A-21978.6 consists of sporophores which are of the Rectus-Flexibilis (RF) classification. Spore chains have >10 spores per chain. Spore surface is smooth.

Culture A-21978.6 is characterized by the production of a predominantly red aerial spore mass color, with a reddish-brown reverse color. A light-brown water-soluble pigment is also present. These characteristics are exhibited on three of 14 agar plating media (ISP #2, ISP #7, TPO). These three media are the only ones which supported abundant aerial and vegetative growth.

Two agar plating media, ISP #4 and glucose-asparagine agar, produced a white-to-gray aerial spore mass color, with a yellow reverse color. No water-soluble pigment was observed. These two media supported good, but not abundant, aerial and vegetative growth.

Nine other agar plating media were used, but these gave poor-to-no growth and sporulation. Aerial color when present, although poor, was in the white-to-gray color series.

Melanoid pigments are absent. Major constituents of the cell wall are: LL-DAP, glycine, glucose, and ribose. This indicates a Type I cell wall, and type C sugar pattern (R. E. Buchanan, and N. E. Gibbons, Eds., "Bergey's Manual of Determinative Bacteriology," The Williams & Wilkins Company, 8th Edition, 1974, p. 658).

The following five cultures were compared in laboratory tests to A-21978.6:
*Streptomyces albovinaceous* ISP 5136; ATCC 15833
*Streptomyces candidus* ISP 5141; ATCC 19891
*Streptomyces moderatus* ISP 5529; ATCC 23443
*Streptomyces roseosporus* ISP 5122; ATCC 23958
*Streptomyces setonii* ISP 5395; ATCC 25497

These cultures belong to the white and red color series, have RF type sporophore morphology, smooth spore surface ornamentation, and, according to the ISP descriptions, are melanin negative and do not have a distinctive reverse color or water-soluble pigments. These characteristics, together with carbon-utilization pattern and other secondary features, match those of culture A-21978.6.

When these cultures were compared with A-21978.6 under laboratory conditions, four were rejected. *S. candidus* and *S. setonii* exhibited a yellow aerial spore mass on many media, thereby differing from culture A-21978.6. *S. albovinaceous* and *S. moderatus* exhibited dark distinctive reverse color, water-soluble pigments, and produced melanoid pigments, all of which were different from culture A-21978.6. The ISP description of *S. moderatus* refers to reddish brown or strong-brown reverse color, but does not refer to such a characteristic for *S. albovinaceous*. Neither culture is listed as melanin positive.

Culture A21978.6 was classified, therefore, as a strain of *Streptomyces roseosporus*, Falcão de Morias and Daliá Maia 1961. This classification was based on comparison with published descriptions and direct laboratory comparisons. The following cultural characteristics summarize the direct comparison studies.

| Cultural Characteristics | | | |
|---|---|---|---|
| A21978.6 | | *S. roseosporus* | |
| Morphology | | | |
| Sporophores straight to flexuous (RF), with no hooks, loops or spirals observed. | | | |
| Chains of spores >10. The spore surface smooth as determined by scanning electron microscopy. | | | |
| Spores: Oblong to oval | | Oblong to cylindrical | |
| Average: 0.85 × 1.78 μM | | 1.01 × 2.47 μM | |
| Range: 0.65–0.97 × 0.97–2.6 μM | | 0.97–1.3 × 1.63–3.25 μM | |
| Growth | Color | Growth | Color |
| Carrot Plugs | | | |
| Aerial: good | gray c̄ pink | none | none |
| Vegetative: abundant | brown | good | yellow-brown |
| no soluble pigment | | no soluble pigment | |
| Potato Plugs | | | |
| Aerial: good | gray c̄ pink | none | none |
| Vegetative: abundant | brown | fair | orange-brown |
| dark brown soluble pigment | | no soluble pigment | |
| ISP #1 (Tryptone-yeast ext. agar) | | | |
| Aerial: fair | (W)a white | poor | (W)a white |
| Vegetative: good | [10A1] pale yellow green | poor | [10B2] pale yellow green |
| no soluble pigment | | no soluble pigment | |
| ISP #2 (Yeast-malt extract agar) | | | |
| Aerial: abundant | (R) 5cb gy. yellow pink | abundant | (R) 3ca pale orange yellow |
| Vegetative: abundant | [5D10] lt. red brown | abundant | [12L7] lt. olive brown |
| light brown soluble pigment | | light brown soluble pigment | |
| ISP #3 (Oatmeal agar) | | | |
| Aerial: fair | (W)a white | poor | (W)a white |
| Vegetative: fair | [10A2] pale yellow pink | fair | pale greenish gray |
| light brown soluble pigment | no soluble pigment | | |
| ISP #4 (Inorganic salts starch agar) | | | |
| Aerial: good | (W)b white | good | (R) 3c2 pale orange yellow |
| Vegetative: good | [10B1] pale yellow-green | abundant | [1I5] grayish yellow |
| light brown soluble pigment | | no soluble pigment | |
| ISP #5 (Glycerol - asparagine agar) | | | |
| Aerial: fair | (W) 13ba purplish white | fair | (W)b white |
| Vegetative: good | [3B7] gy. yellow pink | good | [10C2] grayish yellow |
| gy. pink soluble pigment | | light brown soluble pigment | |
| ISP #7 (Tyrosine agar) | | | |
| Aerial: abundant | (R) 5cb gy. yellow pink | abundant | (R) 5cb gy. yellow pink |
| Vegetative: abundant | [7L12] mod. red brown | abundant | [11E5] yellow-brown |
| dark brown soluble pigment | | light brown soluble pigment | |
| Bennett's modified agar | | | |
| Aerial: none | — | abundant | (R) 5cb gray yellow pink |
| Vegetative: poor | pale yellow brown | abundant | [11D4] grayish yellow |
| no soluble pigment | | light brown soluble pigment | |
| Calcium malate agar | | | |

4,800,157

-continued

| | | | |
|---|---|---|---|
| Aerial: none | — | poor | (W)a white |
| Vegetative: fair | [7L12] mod. red brown | poor | pale yellow-green |
| light brown soluble pigment | | pale yellow-green soluble pigment | |

Czapek's solution agar

| | | | |
|---|---|---|---|
| Aerial: poor | (W)a white | none | — |
| Vegetative: poor | off white | none | — |
| no soluble pigment | | | |

Emerson's agar

| | | | |
|---|---|---|---|
| Aerial: poor | — | abundant | (R) 5cb gy. yellow pink |
| | no soluble pigment | light brown soluble pigment | |

Glucose - asparagine agar

| | | | |
|---|---|---|---|
| Aerial: good | (W)b white | fair | (W)b white |
| Vegetative: good | [12B2] gy. yellow | good | [12B2] pale yellow green |
| no soluble pigment | | no soluble pigment | |

Glycerol - glycine agar

| | | | |
|---|---|---|---|
| Aerial: poor | — | abundant | (W)b white |
| Vegetative: abundant | [8L12] dark gy. brown | abundant | [10G3] light yellow |
| brown soluble pigment | | light brown soluble pigment | |

Nutrient agar

| | | | |
|---|---|---|---|
| Aerial: none | — | fair | (W)b white |
| Vegetative: poor | pale yellow-gray | good | pale yellow gray |
| no soluble pigment | | no soluble pigment | |

Tomato-paste Oatmeal agar

| | | | |
|---|---|---|---|
| Aerial: abundant | (R) 5cb gy. yell. pink | | |
| Vegetative: abundant | [8L12] dk. gy. brown | abundant | [12L7] yellow brown |
| brown soluble pigment | | brown soluble pigment | |

Carbon Utilization

| Substrate | A21978.6 | S. roseosporus |
|---|---|---|
| L-Arabinose | + | + |
| D-Fructose | + | — |
| D-Galactose | + | + |
| D-Glucose | + | + |
| i-Inositol | — | — |
| D-Mannitol | + | — |
| D-Raffinose | — | — |
| L-Rhamnose | + | + |
| Salicin | + | + |
| Sucrose | — | — |
| D-Xylose | + | + |

Key:
+ = Positive utilization
− = Negative utilization

| Characteristic | A21978.6 | S. roseosporus |
|---|---|---|
| Melanoid Pigments | | |
| ISP #1 (tryptone-yeast ext.) | — | — |
| ISP #6 (peptone-yeast ext. iron) | — | — |
| ISP #7 (tyrosine agar) | — | — |
| ISP #7 mod. (ISP #7 minus tyrosine) | — | — |
| Tyrosine assay | — | — |
| Gelatin liquefaction | + | + |
| Skim milk action | slight hydrolysis | slight hydrolysis |
| Starch hydrolysis | + | + |
| pH range | 5–11 | 5–11 |
| Temperature range | 25–40° C. | 25–45° C. |
| Nitrate reduction | — | + |
| NaCl tolerance; growth up to | 10% | 6% |

Antibiotic Sensitivity

| Antibiotic | Conc./Disc | Class | A21978.6 | S. roseosporus |
|---|---|---|---|---|
| Erythromycin | 15 μg | Macrolide | + | + |
| Cephalothin | 30 μg | β-Lactam | + | + |
| Lincomycin | 2 μg | Glycoside | — | — |
| Nystatin | 100 units | Polyene | — | — |
| Polymyxin B | 300 units | Peptide | + | — |
| Streptomycin | 10 μg | Aminoglycoside | + | + |
| Tetracycline | 30 μg | Tetracycline | + | + |
| Vancomycin | 30 μg | Glycopeptide | + | + |

+ = sensitive (zones of inhibition)
− = (no zones of inhibition)

Certain characteristics of the A21978.6 strain differ from the characteristics published for *S. roseosporus*. Culture A21978.6 differs from the published strain in spore size, carrot- and potato-plug growth, NaCl tolerance, and in nitrate reduction.

The A-21978.65 strain of this invention has the identifying characteristics of the A-21978.6 strain, but differs from it in the amount of A-21978C antibiotics produced. The earlier strain at best produced no more than 100 mcg of A-21978C antibiotics per mL of fermentation medium. The improved A-21978.65 strain of this invention produces at least 2½ times this amount in tank fermentations and has produced as much as 18 times this amount in shake flask fermentation. With this enhanced A-21978C-producing characteristic, the new strain offers a greatly improved method for obtaining these antibiotics.

The new A-21978.65 *Streptomyces roseosporus* strain of this invention has been deposited and made a part of the stock culture collection of the Midwest Area Northern Regional Research Center, U.S. Department of Agriculture, Agricultural Research Service, Peoria, Ill., 61604, from which it is available to the public under the accession number NRRL 15998. The preceding *S. roseosporus* strain A-21978.6 is also available from this culture collection under the accession number NRRL 11379.

As is the case with other organisms, the characteristics of the new A-21978C-producing culture of this invention, *Streptomyces roseosporus* NRRL 15998, are subject to variation. Recombinants, variants and mutants of the NRRL 15998 strain may be obtained by treatment with various known mutagens such as ultraviolet rays, X rays, high-frequency waves, radioactive rays and chemicals. Natural and induced variants, mutants and recombinants of *Streptomyces roseosporus* NRRL 15998 which retain the characteristic of enhanced A-21978C antibiotic production may be used in this invention.

The culture medium used to grow the *Streptomyces roseosporus* NRRL 15998 culture can be any one of a number of media. For economy in production, optimal yield, and ease of product isolation, however, certain culture media are preferred. Thus, for example, a preferred carbon source in large-scale fermentation is tapioca dextrin, although glucose, fructose, galactose, maltose, mannose, cottonseed oil, methyl oleate, glycerol, refined soybean oil, and the like can also be used. A preferred nitrogen source is enzyme-hydrolyzed casein, although soluble-meat peptone, soybean flour, soybean hydrolysate, soybean grits, yeast, amino acids such as L-asparagine and DL-leucine, and the like are also useful. Nutrient inorganic salts which can be incorporated ih the culture media are the soluble salts capable of yielding potassium, ammonium, chloride, sulfate, nitrate and like ions. Among these, $K_2SO_4$ is especially useful for antibiotic production. Molasses ash, ash dialysate and synthetic mineral mix are also useful.

For production of the A-21978C antibiotics, it is preferable to use distilled or deionized water in the fermentation medium. Some of the minerals in tap water, such as, for example, calcium and carbonate, appear to discourage antibiotic production.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (e.g., 0.2 ml/L.) of an antifoam agent such as polypropylene glycol to large-scale fermentation media if foaming becomes a problem.

For production of substantial quantities of the A-21978C antibiotics, submerged aerobic fermentation in tanks is preferred. Small quantities of the A-21978C antibiotics may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank.

The new A-21978C-producing organism can be grown at temperatures between about 20° and about 40° C. Optimum A-21978C production appears to occur at temperatures of about 30°-32° C.

As is customary in aerobic submerged culture processes, sterile air is dispersed through the culture medium. For efficient production of the A-21978C antibiotics, the percent of air saturation for tank production should be above 20%, preferably above 30% (at 30° C. and one atmosphere of pressure).

For tank fermentation, it is preferable to maintain the pH level of the fermentation medium in a range of from about 6.5-7.0. This can be done by the addition of appropriate amounts of, for example, sodium hydroxide (in the early stages) and hydrochloric acid (in the later stages).

Production of the A-21978C antibiotics can be followed during the fermentation by testing samples of the broth or of extracts of the mycelial solids for antibiotic activity against organisms known to be sensitive to the antibiotics. One assay organism useful in testing these antibiotics is *Micrococcus luteus*. The bioassay is preferably performed by paper-disc assay on agar plates.

Alternatively, the culture solids, including medium constituents and mycelium can be used without extraction or separation, but preferably after removal of water, as a source of the A-21978C antibiotics. For example, after production of A-21978C antibiotic activity, the culture medium can be dried by lyophilization and mixed directly into feed premix.

In order to illustrate the operation of this invention more fully, the following example is provided.

EXAMPLE 1

Production of the A-21978C Complex

A stock culture is prepared and maintained in the vapor phase of liquid nitrogen. *Streptomyces roseosporus* NRRL 15998 previously stored in the vapor phase of liquid nitrogen was used to inoculate 50 ml of vegetative medium of the following composition:

| Ingredient | Amount (%) |
| --- | --- |
| Trypticase Soy Broth* | 3.0 |
| Dextrin | 2.5 |
| Water (deionized) | 94.5 |

*Baltimore Biological Laboratories, Cockeysville MD.

The inoculated medium was incubated in a 250-ml Erlenmeyer flask at 30° C. for 48 hours on a shaker rotating through an arc of two inches at 250 RPM. The mature vegetative culture was dispensed into multiple containers (0.5 ml/container) and stored in the vapour phase of liquid nitrogen.

In order to provide a larger uniform supply of stored material, one ml of the culture stored in liquid nitrogen was used to inoculate 80 ml of the vegetative medium described above. The inoculated vegetative medium was incubated in a 250-ml Erlenmeyer flask at 30° C. for 48 hours on a shaker rotating through an arc two inches in diameter at 250 RPM.

Ten ml of such a culture was used to inoculate 450 ml of a second-stage vegetative growth medium having the same composition as the primary vegetative medium described supra. The second-stage medium was incubated in a 2-liter Erlenmeyer flask for 24 hours at 30° C. on a shaker rotating through an arc of 2 inches at 250 RPM.

One liter of the second-stage vegetative culture was used to inoculate 39 liters of sterile tertiary inoculum development medium having the following composition:

| Ingredient | Amount (%) |
| --- | --- |
| Soybean Flour | 0.5 |
| Yeast Extract[a] | 0.5 |
| Calcium Gluconate | 1.0 |
| KCl[b] | 0.02 |
| $MgSO_4.7H_2O$[b] | 0.02 |
| $FeSO_4.7H_2O$[b] | 0.0004 |
| Sag 471 (antifoam)[c] | 0.03 |
| Water | 97.9296 |

[a]Difco Laboratories, Detroit, MI.
[b]Trace minerals were prepared as follows: $FeSO_4.7H_2O$ (7.6 g) was dissolved in conc. HCl (76 ml). $MgSO_4.7H_2O$ (380 g), KCl (380 g) and deionized water were added to bring the total volume to 3800 ml. To provide the specified minerals, use 80 ml of solution per 39 liters of tertiary inoculum development stage.
[c]Union Carbide, Danbury, CT.

The inoculated medium was incubated 24 hours in a stainless steel vessel at 30° C. The vessel was aerated with sterile air at 0.85 v/v/m and stirred with conventional agitators at 350–450 RPM. The pressure on the vessel was maintained at 5 PSIG.

One liter of the incubated tertiary inoculum stage was used to inoculate 119 liters of sterile production medium having the following composition:

| Ingredient | Amount (%) |
| --- | --- |
| Soybean Flour | 2.2 |
| $Fe(NH_4)_2SO_4.6H_2O$ | 0.066 |
| Dextrose | 0.825 |
| Sag 471 | 0.022 |
| Potato Dextrin | 3.3 |
| Molasses (blackstrap) | 0.275 |
| Tap Water | 93.312 |

The pH was adjusted to 7.0 after addition of the first two ingredients and again after addition of all the ingredients immediately prior to sterilization.

The inoculated production medium was incubated 6 days in a stainless steel vessel at 30° C. and aerated with sterile air at a rate of 0.5 v/v/m. The medium was stirred with conventional agitators at 250 RPM from 0 to 15 hours and at 350 RPM after 15 hours. The pH was maintained at or above 6.5 by addition of ammonium hydroxide solution. The yield of A-21978C complex was 0.282 grams per liter of broth at the end of the fermentation. The factor distribution is described in Table 1.

TABLE 1

| Distribution of A-21978C Factors Produced by NRRL 15998 | | | | |
| --- | --- | --- | --- | --- |
| A-21978C Factor (μg/ml)[a] | | | | |
| $C_0$ | $C_1$ | $C_2$ | $C_3$ | $C_5$ |
| 12 | 77 | 113 | 72 | 7 |

[a]The concentration of the antibiotic components in filtered broth was estimated by high performance liquid chromatography; the various components were detected by ultraviolet light absorption.

EXAMPLE 2

Shake-Flask Production of the A-21978C Complex

Using the general procedure described in Example 1, but under shake flask conditions with the following fermentation medium:

| Ingredient | Amount (g/L) |
| --- | --- |
| Glucose | 7.5 |
| Dextrin[a] | 30 |
| Enzyme-hydrolyzed casein[b] | 5 |
| Peptone[c] | 5 |
| Molasses | 2.5 |
| Deionized water | q.s. to 1 L |

[a]Stadex 11, A. E. Staley Co., Decatur IL
[b]NZ Amine A, Humko Sheffield Chemical, Lyndhurst NJ
[c]Biosate, Baltimore Biological Laboratories, Cockeysville MD The yield of A-21978C complex from this fermentation was 1800 mcg per mL of broth.

I claim:

1. In the process for producing A-21978C antibiotics, the improvement which comprises cultivating *Streptomyces roseosporus* NRRL 15998, or a variant, on a mutant thereof which retains the characteristic of enhanced A-21978C antibiotic production, in a culture medium containing assimilable sources of carbon, nitrogen, and inorganic salts under submerged aerobic fermentation conditions until A-21978C antibiotics are produced.

2. The process of claim 1 which includes the additional step of separating the A-21978C antibiotics as a complex from the culture medium.

3. The process of claim 2 which includes the additional step of separating A-21978C factor $C_0$ from the A-21978C antibiotic complex.

4. The process of claim 2 which includes the additional step of separating A-21978C factor $C_1$ from the A-21978C antibiotic complex.

5. The process of claim 2 which includes the additional step of separating A-21978C factor $C_2$ from the A-21978C antibiotic complex.

6. The process of claim 2 which includes the additional step of separating A-21978C factor $C_3$ from the A-21978C antibiotic complex.

7. The process of claim 2 which includes the additional step of separating A-21978C factor $C_4$ from the A-21978C antibiotic complex.

8. The process of claim 2 which includes the additional step of separating A-21978C factor $C_5$ from the A-21978C antibiotic complex.

9. The process of claim 1 wherein *S. roseosporus* NRRL 15998 is used.

10. A biologically purified culture of the microorganism *Streptomyces roseosporus* NRRL 15998, or a variant, on a mutant thereof which retains the characteristic of enhanced A-21978C antibiotic production.

11. The culture of claim 10 which is *S. roseosporus* NRRL 15998.

* * * * *